(12) United States Patent
Fan

(10) Patent No.: US 7,531,666 B2
(45) Date of Patent: May 12, 2009

(54) METHOD FOR PREPARING 2-(2-PYRIDINYLMETHYLSULFINYL) BENZIMIDAZOLES

(75) Inventor: Chin-Tsai Fan, Tainan Hsien (TW)

(73) Assignee: Syn-Tech Chem. & Pharm. Co., Ltd. (TW)

( * ) Notice: Subject to any disclaimer, the term of this patent is extended or adjusted under 35 U.S.C. 154(b) by 182 days.

(21) Appl. No.: 11/819,179

(22) Filed: Jun. 26, 2007

(65) Prior Publication Data

US 2009/0005570 A1  Jan. 1, 2009

(51) Int. Cl.
*C07D 401/12* (2006.01)
(52) U.S. Cl. .................................. 546/273.7
(58) Field of Classification Search ............... 546/273.7
See application file for complete search history.

(56) References Cited

U.S. PATENT DOCUMENTS

2006/0281782 A1* 12/2006 Cohen et al. ................. 514/303

OTHER PUBLICATIONS

Thakur et al., "WO3-30%, etc.," Tetrahedron: Asymmetry 14 (2003) 407-410.*

* cited by examiner

*Primary Examiner*—Patricia L Morris
(74) *Attorney, Agent, or Firm*—Bacon & Thomas, PLLC

(57) ABSTRACT

The present invention provides a method for preparing an antiulcer agent, 2-(2-pyridinylmethylsulfinyl)benzimidazoles, such as Omeprazole, Lansoprazole, Pantoprazole and Rabeprazole, which includes oxidizing an intermediate having a linkage of methylthio group (—$CH_2S$—) to methylsulfinyl (—$CH_2S(O)$—) in the presence of an oxidation catalyst of an alkali metal salt of tungstate at a temperature of 10-50° C.

19 Claims, No Drawings

METHOD FOR PREPARING 2-(2-PYRIDINYLMETHYLSULFINYL) BENZIMIDAZOLES

FIELD OF THE INVENTION

The present invention provides a method for preparing an antiulcer agent, 2-(2-pyridinylmethylsulfinyl)benzimidazoles, such as Omeprazole, Lansoprazole, Pantoprazole and Rabeprazole, and particularly to a preparation method having an improved yield at a lower cost.

BACKGROUND OF THE INVENTION

Many patents have disclosed a series of 2-(2-pyridinylmethylsulfinyl)benzimidazoles as excellent agents for inhibiting the secretion of gastric acid, for example 5-methoxy-2-[[(4-methoxy-3,5-dimethyl-2-pyridinyl)methyl]sulfinyl]-1H-benzimidazole (generic name: Omeprazole), 2-[[3-methy-4-(2,2,2-trifluoroethoxy)-2-pyridinyl]methylsulfinyl]-1H-benzimidazole (generic name: Lansoprazole), 5-difluoromethoxy-2-[[(3,4-dimethoxy-2-pyridinyl-methyl)sulfinyl]-1H-benzimidazole] (generic name: Pantoprazole), and 2-[[[4-(3-methoxy)propoxy]-3-methyl-2-pyridinyl]methyl]sulfinyl]-1H benzimidazole (generic name: Rabeprazole). One common technical feature for the preparation of these benzimidazole compounds includes that individual precursors 1, 2, 3 or 4 need to undergo similar oxidation reactions to form sulfinyl final products. According to European Patent EP0302720, a method for preparing Lansoprazole comprises oxidizing 2-[[[3-methyl-4-(2,2,2-trifluoroethoxy)-2-pyridinyl]methyl]thio]-1H-benzimidazole using $H_2O_2$ in the presence of a $V_2O_5$ catalyst. Other than the above-mentioned $V_2O_5/H_2O_2$ method, other oxidation methods for preparing Omeprazole, Lansoprazole, Pantoprazole and Rabeprazole include m-chloroperbenzoic acid (MCPBA) (U.S. Pat. Nos. 4,628,098, 5,386,032, 6,043,371, 6,191,148 and US patent publication No. 2004/0209918 A1), sodium perborate tetrahydrate ($NaBO_3 \cdot 4H_2O$)/$H_2O_2$ [WO99/02521 (1999)], ammonium molybdate (($NH_4$)$_2MoO_4$)/$H_2O_2$ (ES Patent 2,036,948 (1993)), sodium hypochloride (NaClO/TEMPO) [U.S. Pat. No. 6,423,846], Ti(IV)-isoproxide/diisopropylethylamine (U.S. Pat. No. 6,303,788).

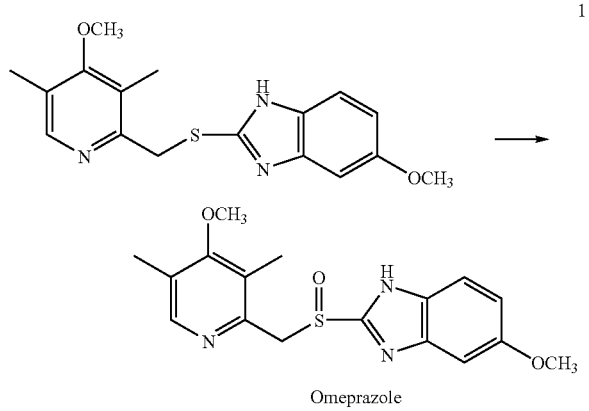

Omeprazole

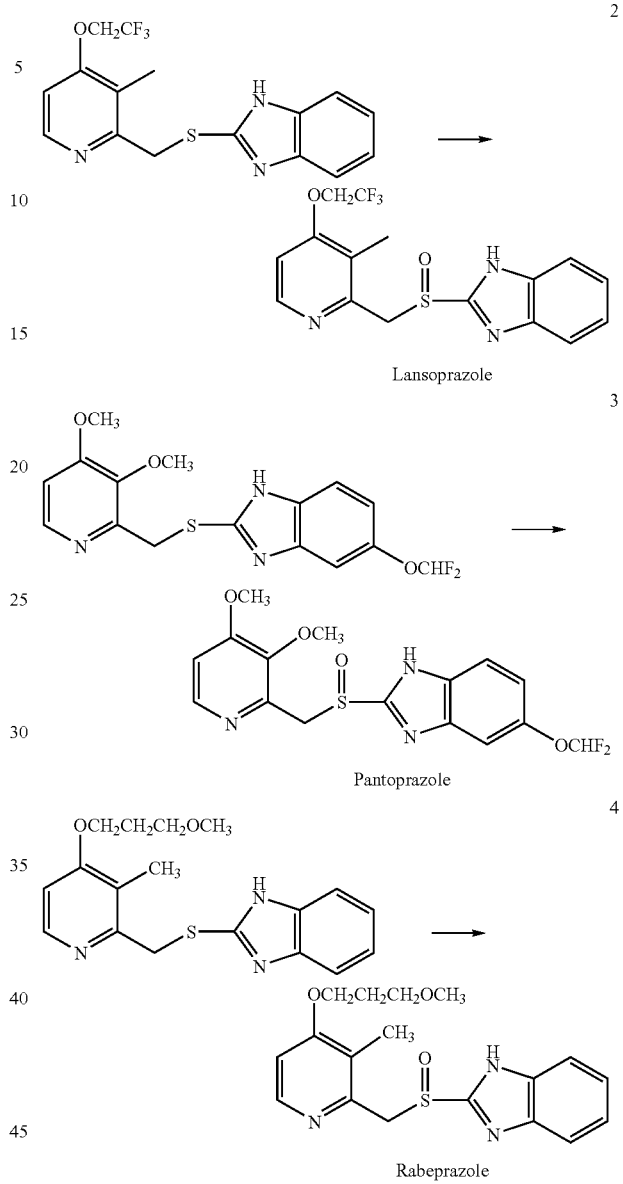

Lansoprazole

Pantoprazole

Rabeprazole

According to prior art, the inventor of the present invention used $V_2O_5$ as an oxidation catalyst and used $H_2O_2$ for the oxidation reaction of Lansoprazole and Omeprazole. Although the reaction ratio can reach above 90% and the oxidation by-products can be controlled to be within 1-2%, the reaction products are liable to become black and cannot be discolored. Therefore, the method is rather difficult in quality control. MCPBA is a conventional catalyst commonly used in the oxidation production of Omeprazole, Lansoprazole, Pantoprazole, and Rabeprazole, etc. However, when MCPBA is used as an oxidant, the reaction temperature is −20° C.~−60° C., and MCPBA is expensive. Under consideration of the low-temperature reaction condition and the production cost, such a method has substantial difficulties in mass production. The inventor of the present invention also conducted investigations in using $NaBO_3 \cdot 4H_2O/H_2O_2$ for the oxidation reaction of Lansoprazole, wherein, even though the reaction ratio can reach around 90%, excessive amount (5%-10%) of oxidation by-products having the following formula I and II are formed:

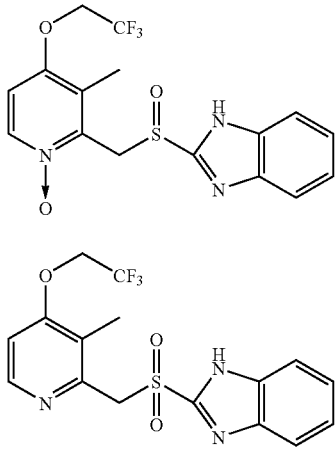

The physical properties of the by-products I and II are rather close to the physical properties of the desired product. Thus, the desired product, after crystallization purification of the reaction product mixture, are rather difficult to be separated from the by-products I and II. If further elaborate purifications are performed, the yield is liable to drop dramatically.

When $(NH_4)_2MoO_4/H_2O_2$ (ES Patent 2,036,948 (1993)) is used as an oxidant rather than $NaBO_3 \cdot 4H_2O/H_2O_2$, more oxidation by-products I and II (8~20%) are produced, and the total yield is about 71-75%. Moreover, the reaction temperature is of 0-5° C. (Examples 16 and 17, ES Patent 2,036,948), which requires additional energy consumption for the low reaction temperature. Thus, such a process is not industrially feasible.

It can be understood from the above that the industry is still looking for a method for commercially mass production of 2-(2-pyridinylmethylsulfinyl)benzimidazoles, such as Omeprazole, Lansoprazole and Pantoprazole, with mild reaction conditions, capable of effectively inhibiting excessive formation of the oxidation by-products I and II, and simple in purification of the desired products.

SUMMARY OF THE INVENTION

A primary objective of the present invention is to provide a method for preparing 2-(2-pyridinylmethylsulfinyl)benzimidazole having the following formula [A], which can be carried out at room temperature with a catalyst which is relatively much lower in price and has an improved yield, thereby making the method of the present invention very cost effective.

The present invention discloses a method for preparing 2-(2-pyridinylmethylsulfinyl)benzimidazole having the following formula [A], which comprises undergoing an oxidation reaction of an intermediate having the following formula [B] in a solvent and in the presence of a catalyst, an oxidant and a base to form the compound [A]:

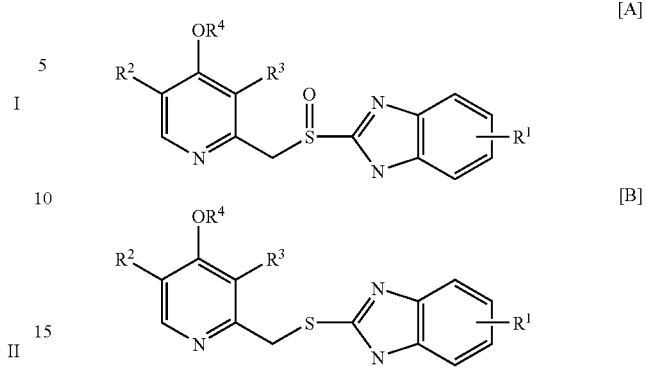

wherein $R^1$ in [A] and [B] is hydrogen, halogen, C1-C6 alkyl, C1-C6 alkoxy, halogenated C1-C6 alkyl, or halogenated C1-C6 alkoxy; $R^2$ and $R^3$ independently are hydrogen, halogen, C1-C6 alkyl, C1-C6 alkoxy, halogenated C1-C6 alkyl, or halogenated C1-C6 alkoxy; and $R^4$ is hydrogen, halogen, C1-C6 alkyl, halogenated C1-C6 alkyl, C1-C6 alkoxy, or halogenated C1-C6 alkoxy;

characterized in that said catalyst comprises an alkali metal salt of tungstate, preferably $Na_2WO_4 \cdot 2H_2O$; and said oxidation reaction is carried out at a temperature of 10-50°° C., preferably at room temperature.

Preferably, said base is an aqueous solution of NaOH, KOH, $Na_2CO_3$, or $K_2CO_3$.

Preferably, said oxidant is $H_2O_2$, tert-butylhydroperoxide, or cumene hydroperoxide, and more preferably $H_2O_2$.

Preferably, said solvent is C1-C6 alcohol, chlorinated C1-C4 alkane, ethyl acetate, toluene, dioxane, acetonitrile, acetone, methylethylketone or tetrahydrofuran. More preferably, said solvent is methanol.

Preferably, said oxidation reaction is carried out in a homogeneous phase solvent or a two-phase solvent.

Preferably, said oxidation reaction is carried out in the two-phase solvent, and an interphase transfer catalyst is added to the two-phase solvent, so that the oxidation reaction is carried out under the presence of said interphase transfer catalyst, wherein said interphase transfer catalyst is selected from the group consisting of quaternary ammonium salt, quaternary phosphate salt, polyether, and crown ether.

Preferably, an equivalent molar ratio of said base to said intermediate [B] is 5:1 to 1:1.

Preferably, a weight ratio of said solvent to said intermediate [B] is 2:1 to 20:1 in the oxidation reaction.

Preferably, a mole ratio of said oxidant to said intermediate [B] is 1:1 to 5:1 in the oxidation reaction.

Preferably, a weight ratio of said catalyst to said intermediate [B] is 3% to 20% in the oxidation reaction.

Preferably, said compound [A] is Lansoprazole.
Preferably, said compound [A] is Omeprazole.
Preferably, said compound [A] is Pantoprazole.
Preferably, said compound [A] is Rabeprazole.

The present invention adopts an alkali metal salt of tungstate as a catalyst, e.g. $Na_2WO_4 \cdot 2H_2O$, together with an oxidant, for the oxidation reaction of the precursors of benzimidazole compounds, such as Omeprazole, Lansoprazole, Pantoprazole and Rabeprazole. According to the present invention, the reaction conditions are mild without severe temperature conditions. Furthermore, the $Na_2WO_4 \cdot 2H_2O$ catalyst is less expensive than the $(NH_4)_2MoO_4$ catalyst.

Most importantly, the reaction produces a rather small amount of the by-products I and II (less than 5%). Accordingly, a preparation method according to the present invention is far superior in comparison to the conventional preparation methods. Thus, the method for preparing a thio-containing antiulcer agent, such as Omeprazole, Lansoprazole Pantoprazole and Rabeprazole, according to the present invention is improved over the conventional methods and applicable for mass production.

DETAILED DESCRIPTION OF THE INVENTION

A method according to the present invention comprises preparing precursor intermediates 1, 2, 3, 4 of Omeprazole, Lansoprazole, Pantoprazole and Rabeprazole; preparing a suitable solvent such as methanol, ethanol, propanol, isopropanol, tetrahydrofuran, acetonitrile, acetone, and methylethylketone, or a two-phase solvent of water and ethyl acetate, dichloromethane, dichloroethane, tetrahydrofuran, dioxane, toluene, or ether, wherein an interphase transfer catalyst (e.g. quaternary ammonium salt, polyether, quaternary phosphate salt, or crown ether (preferably polyether, or crown ether)) is added to the two-phase solvent; adding the intermediate and a base such as an aqueous solution of NaOH, KOH, $Na_2CO_3$, or $K_2CO_3$ into the solvent; and finally adding batchwise or in one lot a mixed solution of an oxidant and a catalyst into the resulting mixture to undergo an oxidation reaction at 10-50° C. A suitable oxidant is selected from the group consisting of $H_2O_2$, sodium percarbonate, tert-butylhydroperoxide (abbreviated as TBHP), cumene hydroperoxide, and Fremyl's salt, wherein $H_2O_2$ is preferable.

EXAMPLE 1

2 g of 2-[[(3,5-dimethyl-4-methoxy-2-pyridinyl)methyl]thio]-5-methoxy-1H-benzimidazole was suspended in 36 ml of methanol at room temperature, to which 1.88 g of 45% NaOH in 14 ml water was added while stirring. 0.09 g of $Na_2WO_4 \cdot 2H_2O$ oxidation catalyst was dissolved in 0.74 g $H_2O_2$ (50% aqueous solution), and further diluted with 10 ml of water. The oxidant/catalyst solution was added to the reactant/base solution dropwise so that the addition was completed in about 30 minutes while stirring at room temperature. The reaction was continued for additional 10 minutes while stirring. 10 ml of 10% $Na_2S_2O_3$ aqueous solution was then added, and the resulting mixture was subjected to a reduced pressure to remove methanol therefrom. Finally, a precipitate was formed after adding a diluted acetic acid aqueous solution to a pH value of about 8, which was filtered, water washed, and dried in vacuo to obtain Omeprazole with a yield of about 88% (LC purity>95%).

EXAMPLE 2

The procedures in Example 1 were repeated except that the 1.88 g of 45% NaOH was replaced by 1.93 g of $Na_2CO_3$. Omeprazole yield: 91% (LC purity>95%).

EXAMPLE 3

2 g of 2-[[[3-methyl-4-(2,2,2-trifluoroethoxy)-2-pyridinyl]methyl]thio]-1H-benzimidazole was suspended in 36 ml of methanol at room temperature, to which 1.76 g of 45% NaOH in 14 ml water was added while stirring. 0.09 g of $Na_2WO_4 \cdot 2H_2O$ oxidation catalyst was dissolved in 0.77 g $H_2O_2$ (50% aqueous solution), and further diluted with 10 ml of water. The oxidant/catalyst solution was added to the reactant/base solution dropwise so that the addition was completed in about 30 minutes while stirring at room temperature. The reaction was continued for additional 10 minutes while stirring. 10 ml of 10% $Na_2S_2O_3$ aqueous solution was then added, and the resulting mixture was subjected to a reduced pressure to remove methanol therefrom. Finally, a precipitate was formed after adding a diluted acetic acid aqueous solution to a pH value of about 8, which was filtered, water washed, and dried in vacuo to obtain Lansoprazole with a yield of about 90.8% (LC purity>95%).

EXAMPLE 4

2 g of 5-difluoromethoxy-2-[[(3,4-dimethoxy-2-pyridinyl)methyl]thio]-1H-benzimidazole was suspended in 36 ml of methanol at room temperature, to which 1.69 g of 45% NaOH in 14 ml water was added while stirring. 0.09 g of $Na_2WO_4 \cdot 2H_2O$ oxidation catalyst was dissolved in 0.7 g $H_2O_2$ (50% aqueous solution), and further diluted with 10 ml of water. The oxidant/catalyst solution was added to the reactant/base solution dropwise so that the addition was completed in about 30 minutes while stirring at room temperature. The reaction was continued for additional 10 minutes while stirring. 10 ml of 10% $Na_2S_2O_3$ aqueous solution was then added, and the resulting mixture was subjected to a reduced pressure to remove methanol therefrom. Finally, a precipitate was formed after adding a diluted acetic acid aqueous solution to a pH value of about 8, which was filtered, water washed, and dried in vacuo to obtain Pantoprazole with a yield of about 90.2% (LC purity>95%).

EXAMPLE 5

2 g of 5-difluoromethoxy-2-[[(3,4-dimethoxy-2-pyridinyl)methyl]thio]-1H-benzimidazole was suspended in 36 ml of methanol at room temperature, to which 4.1 g of $Na_2CO_3$ in 14 ml water was added while stirring. 0.09 g of $Na_2WO_4 \cdot 2H_2O$ oxidation catalyst was dissolved in 0.74 g $H_2O_2$ (50% aqueous solution), and further diluted with 10 ml of water. The oxidant/catalyst solution was added to the reactant/base solution dropwise so that the addition was completed in about 30 minutes while stirring at room temperature. The reaction was continued for additional 10 minutes-while stirring. 10 ml of 10% $Na_2S_2O_3$ aqueous solution was then added, and the resulting mixture was subjected to a reduced pressure to remove methanol therefrom. Finally, a precipitate was formed after adding a diluted acetic acid aqueous solution to a pH value of about 8, which was filtered, water washed, and dried in vacuo to obtain Pantoprazole with a yield of about 85% (LC purity>95%).

EXAMPLE 6

2 g of 2-[[[4-(3-methoxy-propoxy)-3-methyl-2-pyridinyl]methyl]thio]-1H-benzimidazole was suspended in 36 ml of methanol at room temperature, to which 1.93 g of 45% NaOH in 14 ml water was added while stirring. 0.09 g of $Na_2WO_4 \cdot 2H_2O$ oxidation catalyst was dissolved in 0.66 g $H_2O_2$ (50% aqueous solution), and further diluted with 10 ml of water. The oxidant/catalyst solution was added to the reactant/base solution dropwise so that the addition was completed in about 30 minutes while stirring at room temperature. The reaction was continued for additional 10 minutes while stirring. 10 ml of 10% $Na_2S_2O_3$ aqueous solution was then added, and the resulting mixture was subjected to a reduced pressure to remove methanol therefrom. Finally, a precipitate was formed after adding a diluted acetic acid aqueous solution to a pH value of about 8, which was filtered, water washed, and dried in vacuo to obtain Rabeprazole with a yield of about 88% (LC purity>95%).

EXAMPLE 7

The procedures in Example 6 were repeated except that the 1.93 g of 45% NaOH was replaced by 4.7 g of $Na_2CO_3$. Rabeprazole yield: 86.8% (LC purity>95%).

CONTROL EXAMPLE 1

0.5 g of 2-[[[3-methyl-4-(2,2,2-trifluoroethoxy)-2-pyridinyl]methyl]thio]-1H-benzimidazole was suspended in 7 ml of ethanol at room temperature. 0.025 g of $Na_2WO_4 \cdot 2H_2O$ oxidation catalyst was dissolved in 0.141 g $H_2O_2$ (35% aqueous solution), and further diluted with 2 ml of water. The oxidant/catalyst solution was added to the reactant suspension dropwise so that the addition was completed in about 30 minutes while stirring at room temperature. The reaction was continued for additional 8 hours while stirring. 2 ml of 10% $Na_2S_2O_3$ aqueous solution was then added, and the resulting mixture was subjected to a reduced pressure to remove ethanol therefrom. Finally, a precipitate was formed after adding a diluted acetic acid aqueous solution to a pH value of about 8, which was filtered, water washed, and dried in vacuo to obtain Lansoprazole with a yield of about 63% (LC purity>80%).

CONTROL EXAMPLE 2

0.35 g of 2-[[(3,5-dimethyl-4-methoxy-2-pyridinyl)methyl]thio]-5-methoxy-1H-benzimidazole was suspended in 5 ml of ethanol at room temperature. 0.035 g of $Na_2WO_4 \cdot 2H_2O$ oxidation catalyst was dissolved in 0.099 g $H_2O_2$ (35% aqueous solution), and further diluted with 2 ml of water. The oxidant/catalyst solution was added to the reactant suspension dropwise so that the addition was completed in about 30 minutes while stirring at room temperature. The reaction was continued for additional 6 hours while stirring. 2 ml of 10% $Na_2S_2O_3$ aqueous solution was then, added, and the resulting mixture was subjected to a reduced pressure to remove ethanol therefrom. Finally, a precipitate was formed after adding a diluted acetic acid aqueous solution to a pH value of about 8, which was filtered, water washed, and dried in vacuo to obtain Omeprazole with a yield of about 69% (LC purity>80%).

CONTROL EXAMPLE 3

0.4 g of 5-difluoromethoxy-2-[[(3,4-dimethoxy-2-pyridinyl)methyl]thio]-1H-benzimidazole was suspended in 6 ml of methanol at room temperature. 0.02 g of $Na_2WO_4 \cdot 2H_2O$ oxidation catalyst was dissolved in 0.109 g $H_2O_2$ (35% aqueous solution), and further diluted with 2 ml of water. The oxidant/catalyst solution was added to the reactant solution dropwise so that the addition was completed in about 30 minutes while stirring at room temperature. The reaction was continued for additional 5.5 hours while stirring. 10 ml of 10% $Na_2S_2O_3$ aqueous solution was then added, and the resulting mixture was subjected to a reduced pressure to remove methanol therefrom, followed by adding a diluted acetic acid aqueous solution to a pH value of about 8. The resulting pH=8 mixture was extracted with ethyl acetate to obtain a crude product of Pantoprazole with a LC purity of about 52.5%.

The invention claimed is:

1. A method for preparing 2-(2-pyridinylmethylsulfinyl)benzimidazole having the following formula [A], which comprises undergoing an oxidation reaction of an intermediate having the following formula [B] in a solvent and in the presence of a catalyst, an oxidant and a base to form the compound [A]:

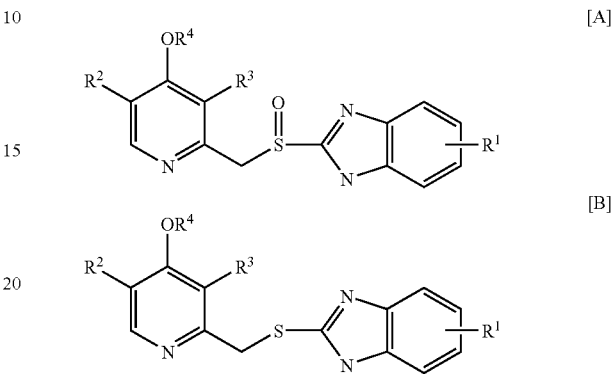

wherein $R^1$ in [A] and [B] is hydrogen, halogen, C1-C6 alkyl, C1-C6 alkoxy, halogenated C1-C6 alkyl, or halogenated C1-C6 alkoxy; $R^2$ and $R^3$ independently are hydrogen, halogen, C1-C6 alkyl, C1-C6 alkoxy, halogenated C1-C6 alkyl, or halogenated C1-C6 alkoxy; and $R^4$ is hydrogen, halogen, C1-C6 alkyl, halogenated C1-C6 alkyl, C1-C6 alkoxy, or halogenated C1-C6 alkoxy;

wherein the improvement comprises said catalyst comprises an alkali metal salt of tungstate; and said oxidation reaction is carried out at a temperature of 10-50° C.

2. The method as claimed in claim 1, wherein said catalyst is $Na_2WO_4 \cdot 2H_2O$.

3. The method as claimed in claim 2, wherein said oxidation reaction is carried out at room temperature.

4. The method as claimed in claim 1, wherein said base is an aqueous solution of NaOH, KOH, $Na_2CO_3$, or $K_2CO_3$.

5. The method as claimed in claim 1, wherein said oxidant is $H_2O_2$, tert-butylhydroperoxide, or cumene hydroperoxide.

6. The method as claimed in claim 5, wherein said oxidant is $H_2O_2$.

7. The method as claimed in claim 1, wherein said solvent is C1-C6 alcohol, chlorinated C1-C4 alkane, tetrahydrofuran, acetonitrile, acetone, methylethylketone, ethyl acetate, dioxane, toluene, or ether.

8. The method as claimed in claim 7, wherein said solvent is methanol.

9. The method as claimed in claim 3, wherein said solvent is methanol, said base is an aqueous solution of NaOH, KOH, $Na_2CO_3$, or $K_2CO_3$, and said oxidant is $H_2O_2$.

10. The method as claimed in claim 1, wherein said oxidation reaction is carried out in a homogeneous phase solvent or a two-phase solvent.

11. The method as claimed in claim 10, wherein said oxidation reaction is carried out in the two-phase solvent, and an interphase transfer catalyst is added to the two-phase solvent, so that the oxidation reaction is carried out under the presence of said interphase transfer catalyst, wherein said interphase transfer catalyst is selected from the group consisting of quaternary ammonium salt, quaternary phosphate salt, polyether, and crown ether.

12. The method as claimed in claim 1, wherein a weight ratio of said solvent to said intermediate [B] is 2:1 to 20:1.

13. The method as claimed in claim 1, wherein a mole ratio of said oxidant to said intermediate [B] is 1:1 to 5:1.

14. The method as claimed in claim 1, wherein a weight ratio of said catalyst to said intermediate [B] is 3% to 20%.

15. The method as claimed in claim 1, wherein an equivalent molar ratio of said base to said intermediate [B] is 5:1 to 1:1.

16. The method as claimed in claim 1, wherein said compound [A] is 2-[[3-methy-4-(2,2,2-trifluoroethoxy)-2-pyridinyl]methylsulfinyl]-1H-benzimidazole.

17. The method as claimed in claim 1, wherein said compound [A] is 5-methoxy-2-[[(4-methoxy-3,5-dimethyl-2-pyridinyl)methyl]sulfinyl]-1H-benzimidazole.

18. The method as claimed in claim 1, wherein said compound [A] is 5-difluoromethoxy-2-[[(3,4-dimethoxy-2-pyridinyl-methyl)sulfinyl)-1H-benzimidazole].

19. The method as claimed in claim 1, wherein said compound [A] is 2-[[[4-(3-methoxy)propoxy]-3-methyl-2-pyridinyl]methyl]sulfinyl]-1H benzimidazole.

\* \* \* \* \*